(12) United States Patent
Richter

(10) Patent No.: US 9,533,300 B2
(45) Date of Patent: Jan. 3, 2017

(54) DELIVERY SYSTEM FOR ANALYTICAL SAMPLES

(76) Inventor: Daniel T. Richter, Aransas Pass, TX (US)

( * ) Notice: Subject to any disclaimer, the term of this patent is extended or adjusted under 35 U.S.C. 154(b) by 2 days.

(21) Appl. No.: 13/385,843

(22) Filed: Mar. 8, 2012

(65) Prior Publication Data

US 2013/0236276 A1    Sep. 12, 2013

(51) Int. Cl.
| | |
|---|---|
| B65G 53/28 | (2006.01) |
| B65G 53/66 | (2006.01) |
| B01L 3/00 | (2006.01) |
| G01N 35/04 | (2006.01) |
| B65G 51/02 | (2006.01) |

(52) U.S. Cl.
CPC ............... *B01L 3/00* (2013.01); *G01N 35/04* (2013.01); *B65G 51/02* (2013.01); *G01N 2035/0465* (2013.01); *G01N 2035/0481* (2013.01)

(58) Field of Classification Search
CPC ............. G01N 35/1095; G01N 2035/0481
See application file for complete search history.

(56) References Cited

U.S. PATENT DOCUMENTS

| | | |
|---|---|---|
| 1,733,026 A | 10/1929 | Guinness |
| 4,478,095 A | 10/1984 | Bradley |
| 4,622,457 A | 11/1986 | Bradley |
| 4,662,231 A * | 5/1987 | Schaarschmidt et al. ...... 73/863 |
| 4,886,401 A | 12/1989 | Andrews |
| 4,941,777 A | 7/1990 | Kieronski |
| 5,234,292 A | 8/1993 | Lang |
| 5,297,922 A | 3/1994 | Sieg |
| 5,337,920 A | 8/1994 | Clausen |
| 5,424,037 A | 6/1995 | Zimmerman |
| 5,441,699 A | 8/1995 | So |
| 5,623,415 A | 4/1997 | O'Brien |
| 5,682,026 A | 10/1997 | Auclair |
| 5,805,454 A | 9/1998 | Valerino |
| 6,071,477 A | 6/2000 | Auclair |
| 6,128,549 A | 10/2000 | Swartz |
| 6,141,602 A | 10/2000 | Igarashi |
| 6,659,693 B1 | 12/2003 | Perkins |
| 6,974,294 B2 | 12/2005 | Pressman |
| 7,228,198 B2 | 6/2007 | Vollm |
| 7,303,094 B2 | 12/2007 | Hutchinson |
| 7,407,627 B1 | 8/2008 | Rosenberg |
| 7,532,948 B2 | 5/2009 | Vollm |

(Continued)

*Primary Examiner* — P. Kathryn Wright
(74) *Attorney, Agent, or Firm* — G. Turner Moller

(57) ABSTRACT

A system for handling sample vials includes a vault for receiving a series of storage cartridges. Inside the cartridges are one or more discs providing vial recesses. In multidisc cartridges, through passages are provided to place and retrieve vials into and from the subjacent discs. A pick up device is moved until it aligns with a selected vial and the vial is pneumatically removed. A device is provided to reverse orientation of a vial moving through the system. A venturi operated system is provided including symmetrical bleed off ports to propel vials through the system without inducing excessive spinning of the vials. A piping system from a central bank to a multiplicity of analytical instruments includes a minimum number of through conduits and a diverter at each instrument location for sending the vial either to the instrument or downstream toward another diverter and instrument.

27 Claims, 12 Drawing Sheets

(56) References Cited

U.S. PATENT DOCUMENTS

| | | |
|---|---|---|
| 7,648,321 B2 | 1/2010 | Neeper |
| 7,753,229 B2 | 7/2010 | Hutchinson |
| 7,789,267 B2 | 9/2010 | Hutchinson |
| 7,824,613 B2 | 11/2010 | Richter |
| 7,831,334 B2 | 11/2010 | Vollm |
| 7,909,207 B2 | 3/2011 | Handfield |
| 7,917,246 B2 | 3/2011 | Handfield |
| 8,066,943 B2 | 11/2011 | Kegelman |
| 8,083,994 B2 | 12/2011 | Neeper |
| 2002/0198738 A1 | 12/2002 | Osbrone |
| 2004/0100415 A1 | 5/2004 | Veitch |
| 2006/0120835 A1 | 6/2006 | Pressman |
| 2006/0210435 A1 | 9/2006 | Alavie |
| 2007/0186514 A1 | 8/2007 | Vollm |
| 2008/0253927 A1 | 10/2008 | Burow |

\* cited by examiner

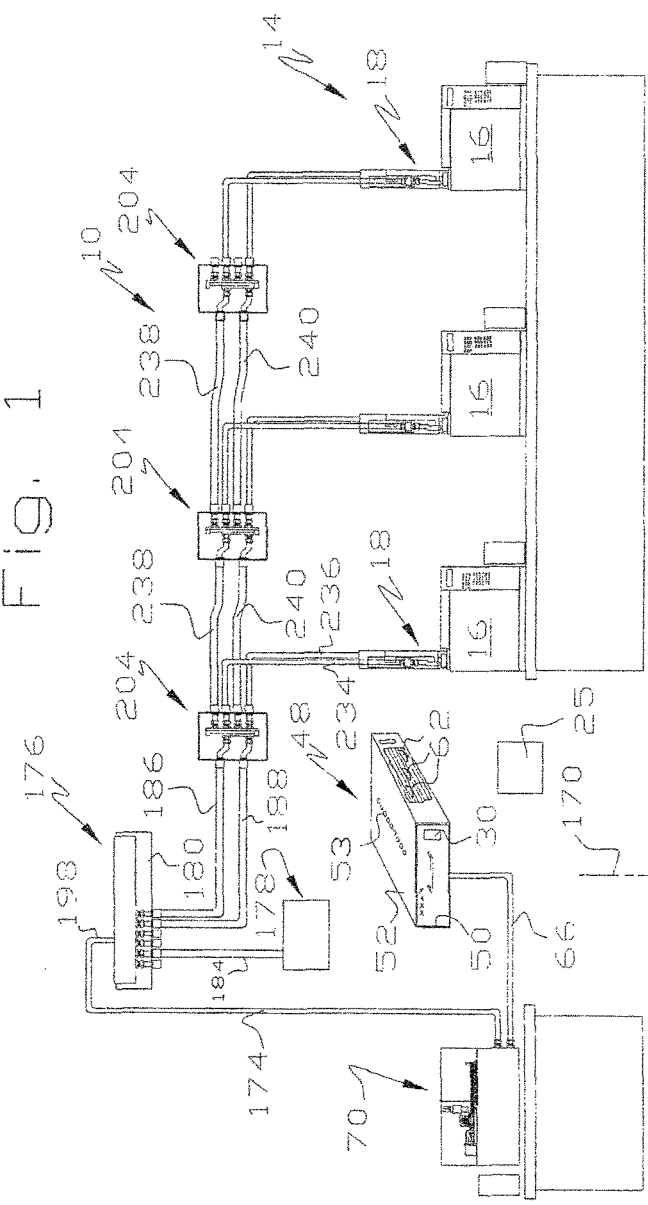

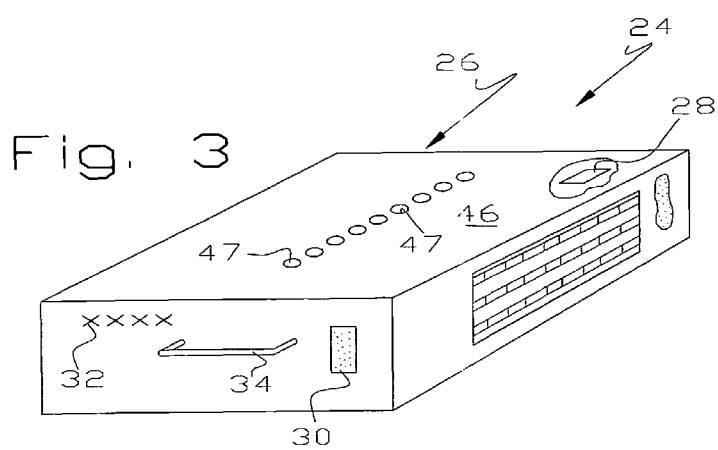
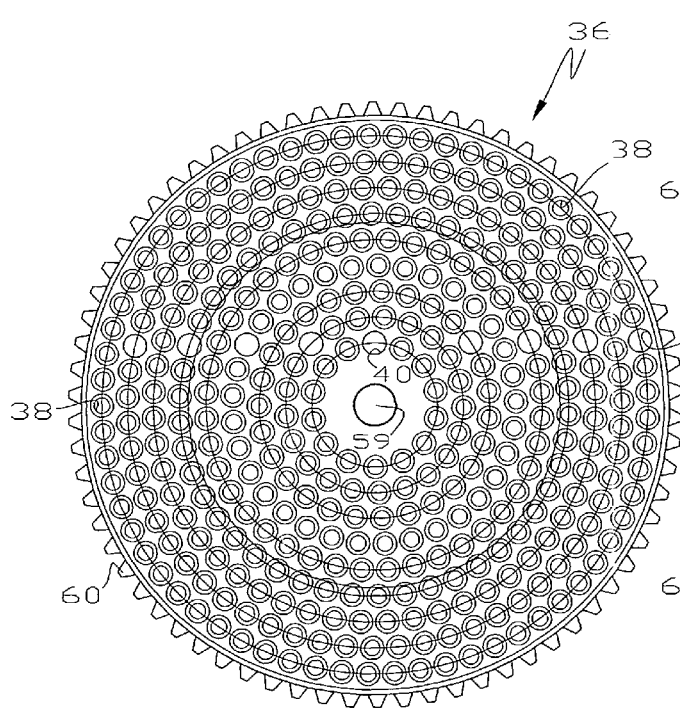
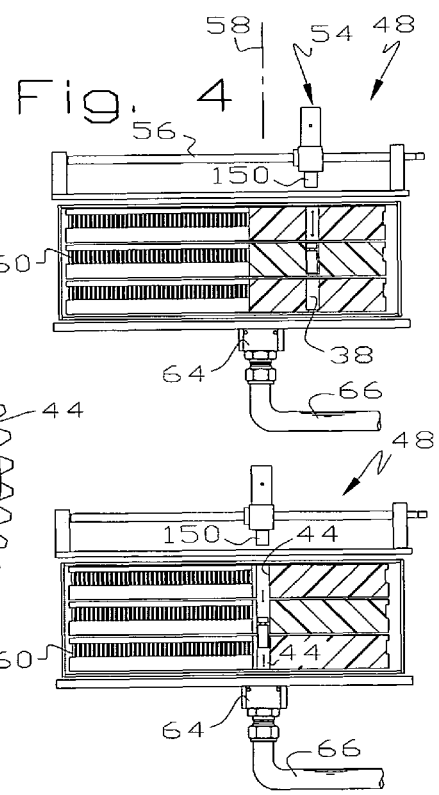

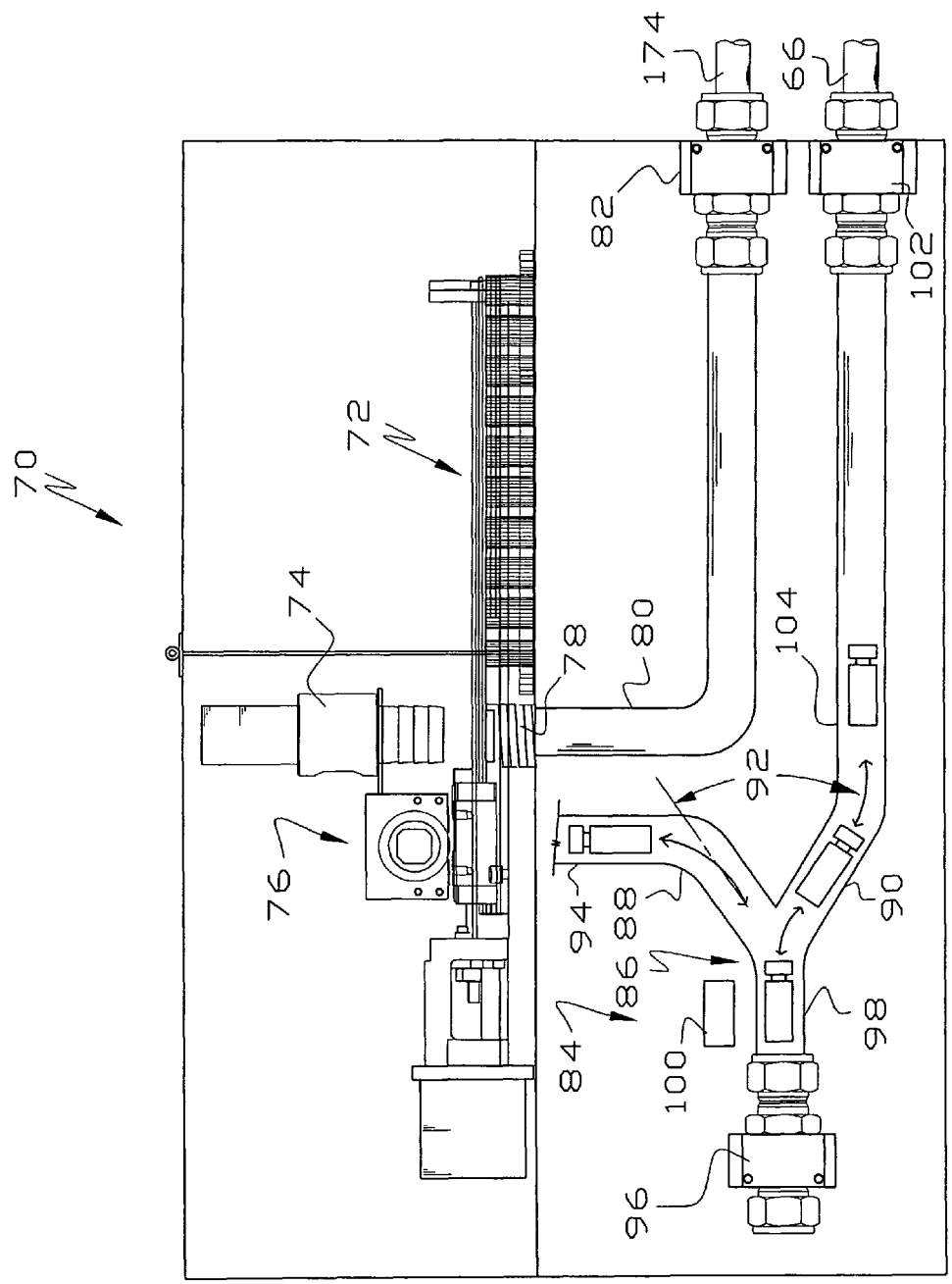

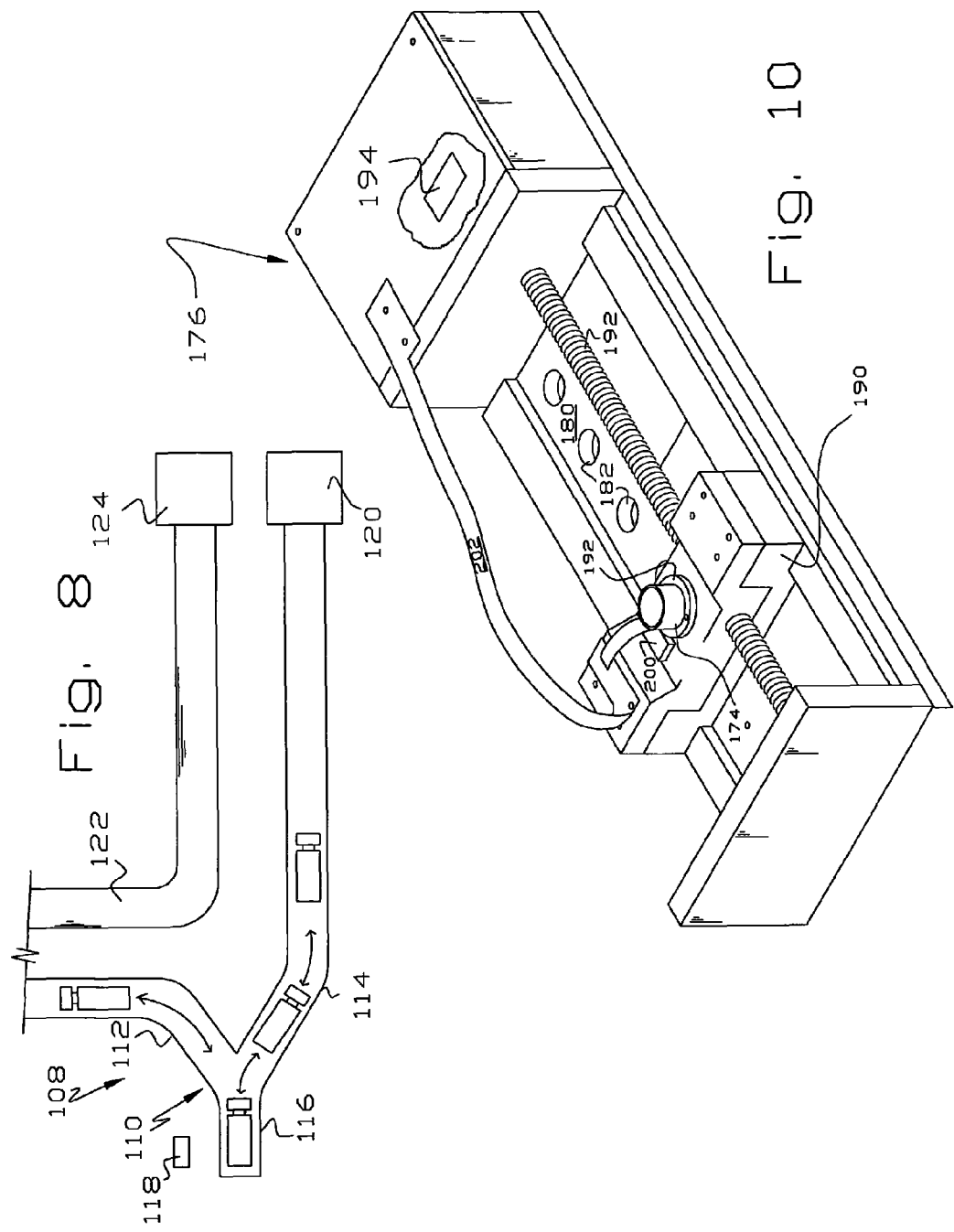

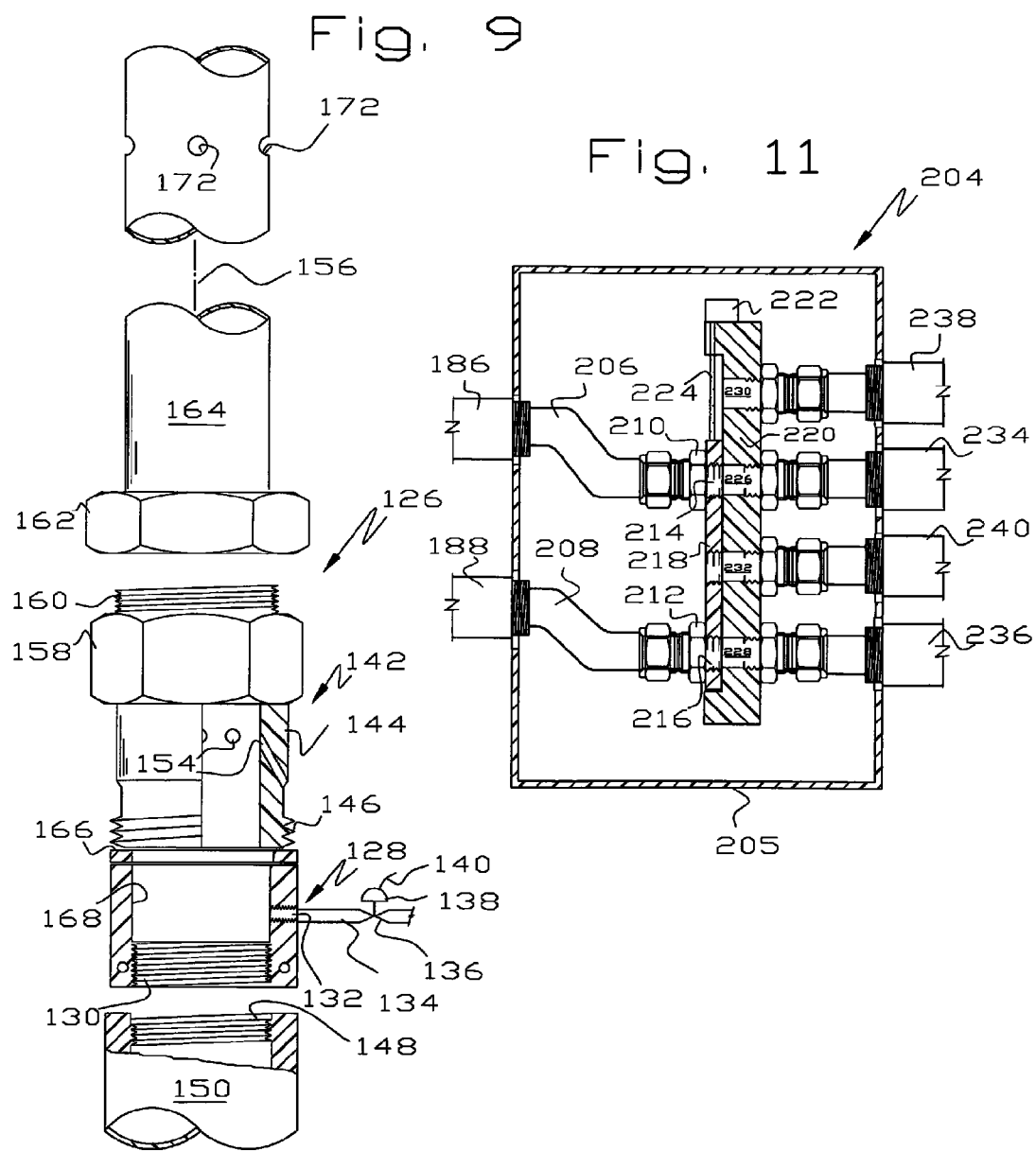

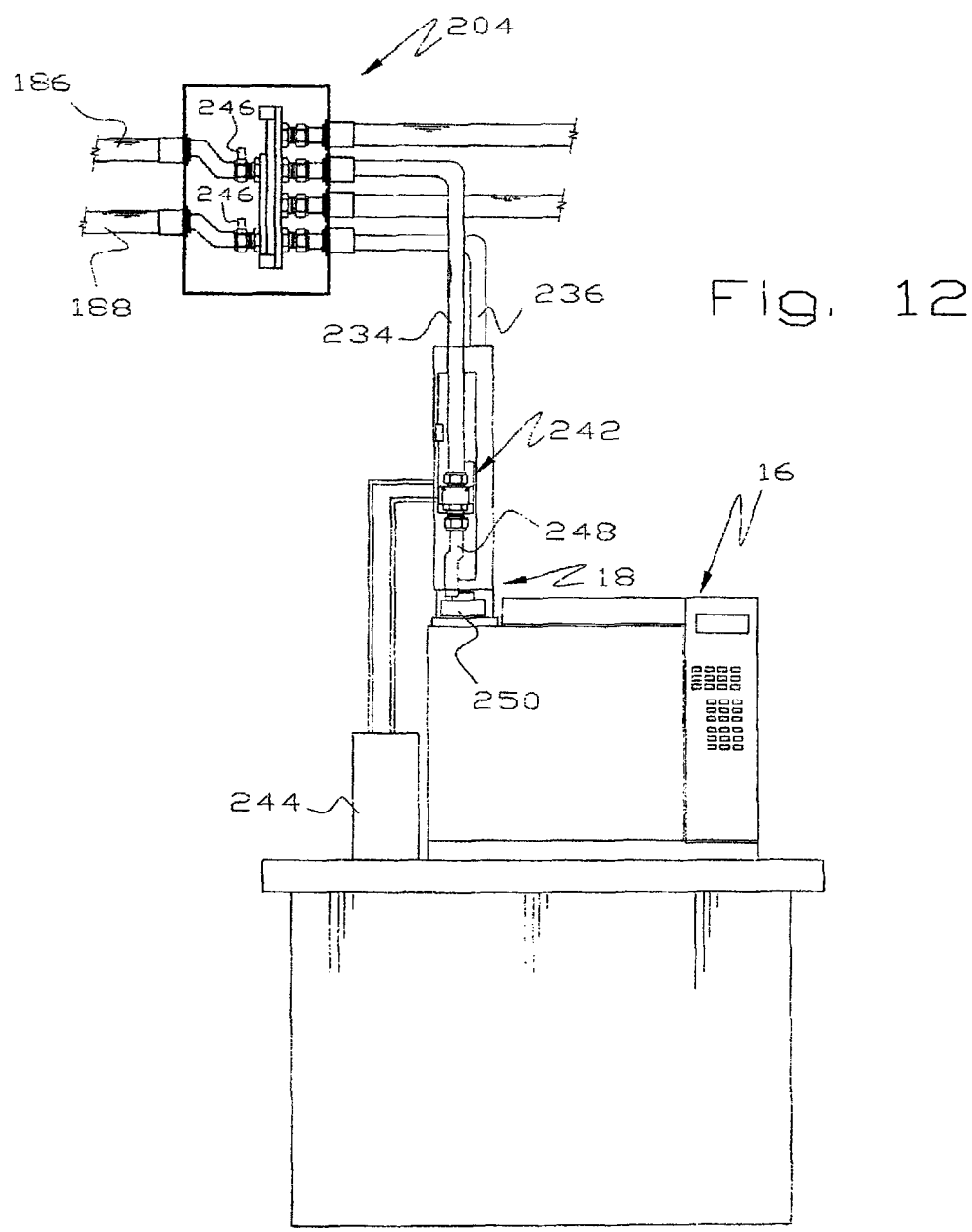

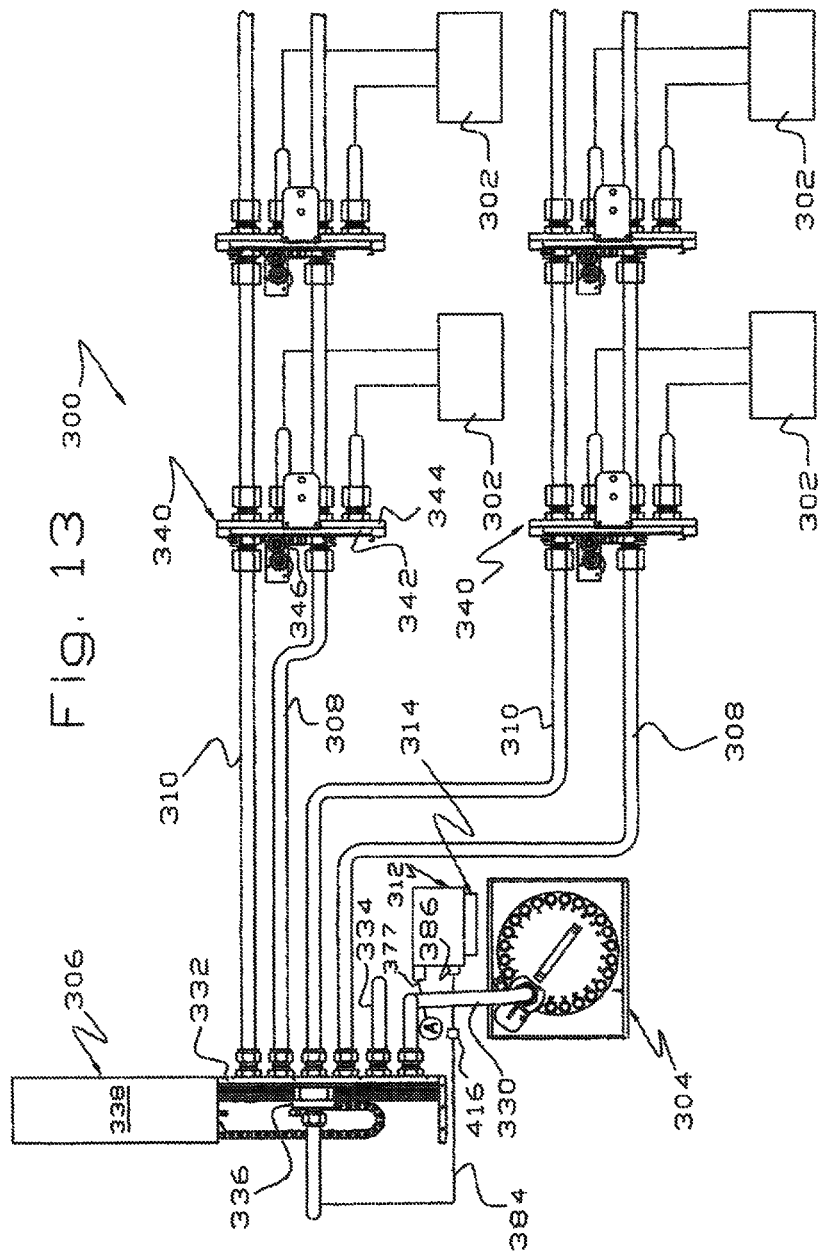

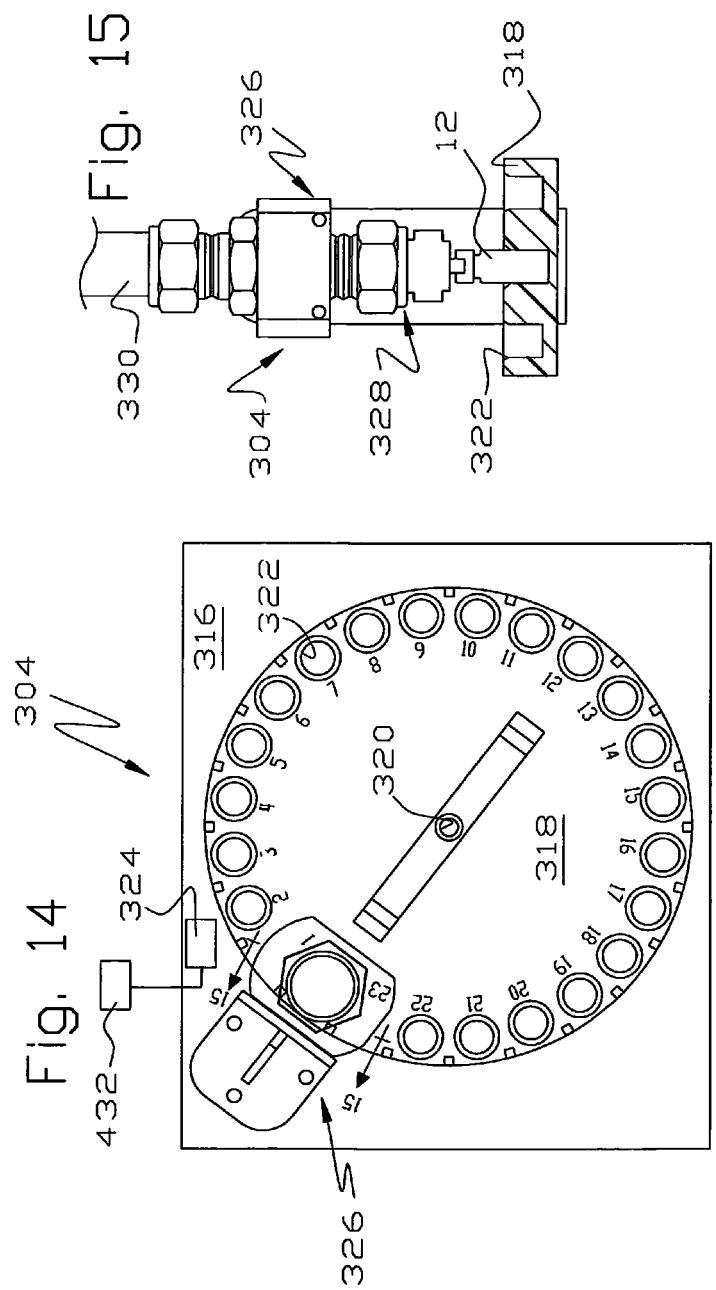

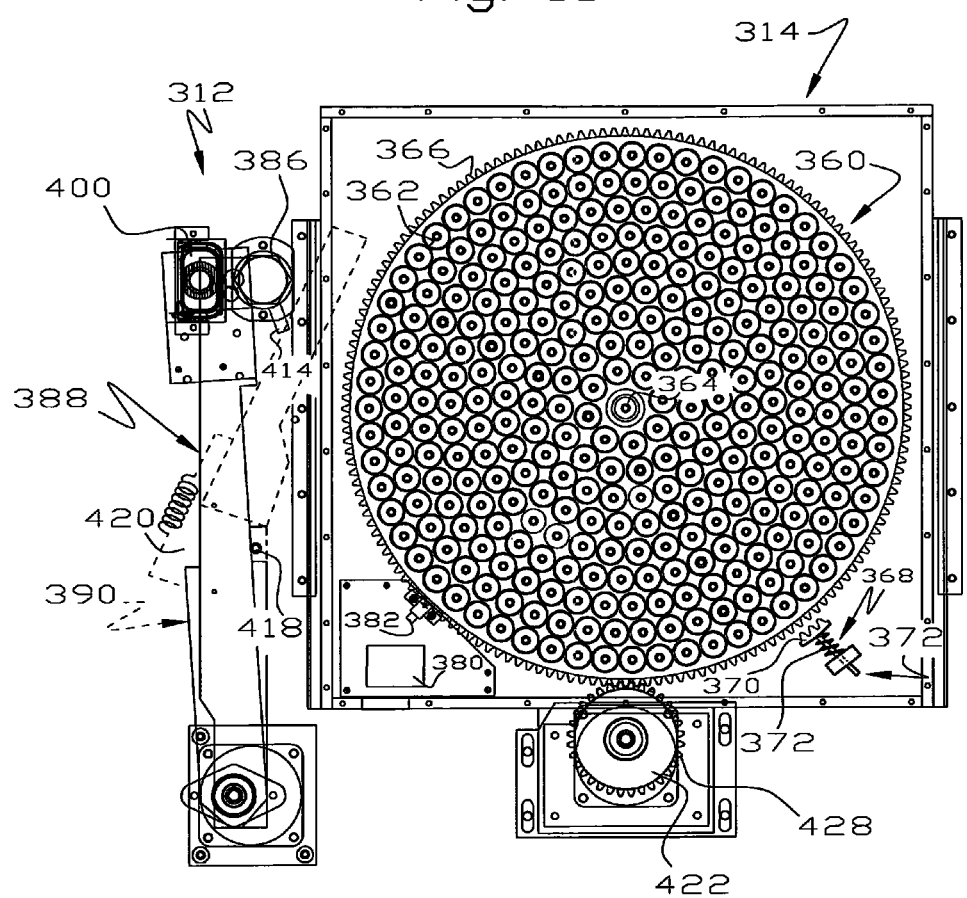

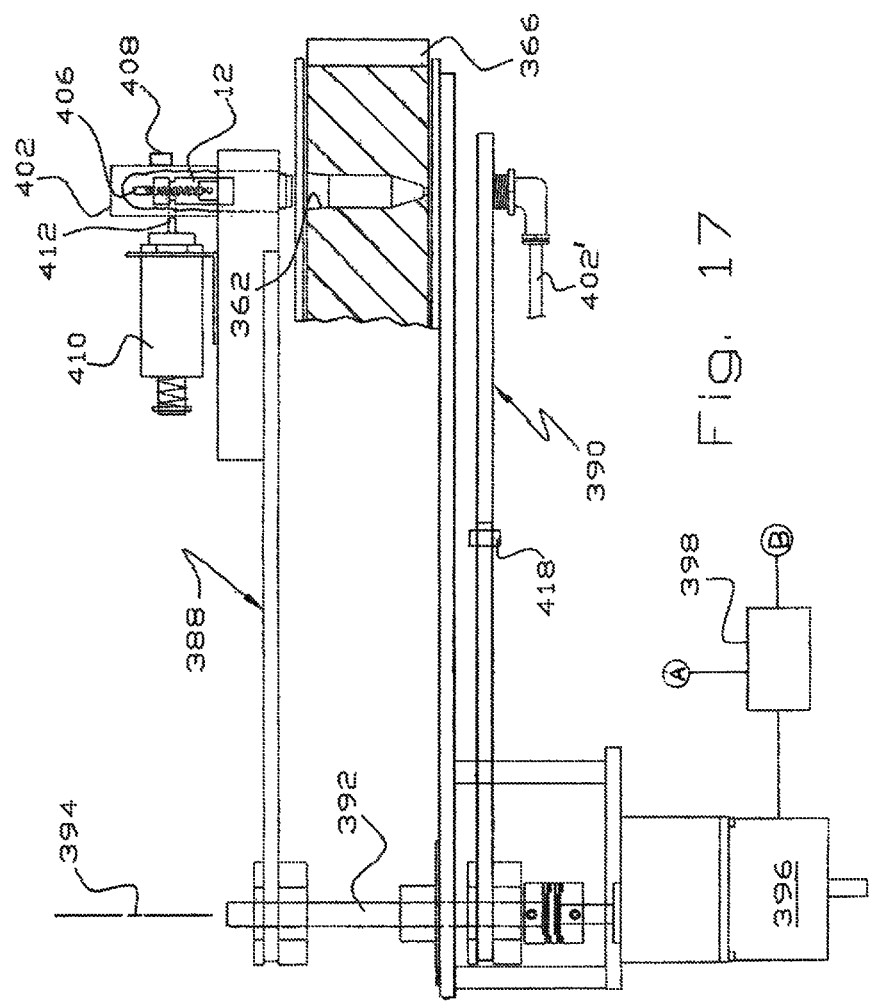

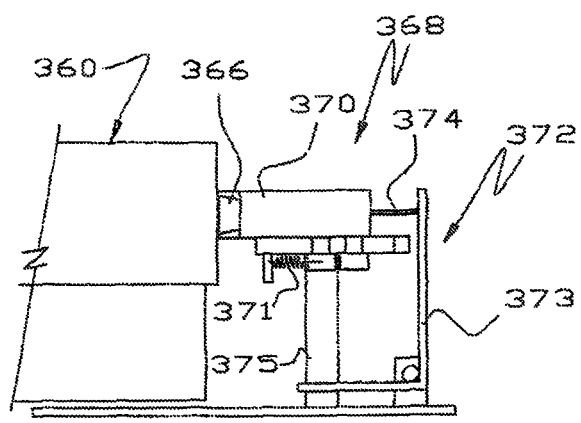
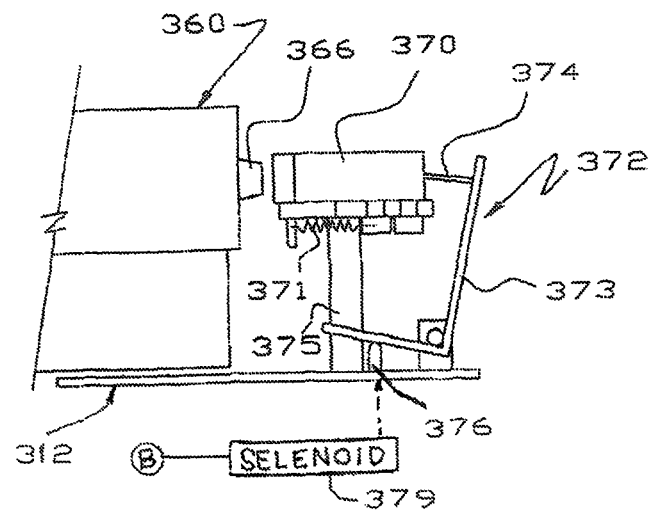

US 9,533,300 B2

DELIVERY SYSTEM FOR ANALYTICAL SAMPLES

This invention relates to a system for delivering samples to analytical instruments, particularly gas chromatographs, mass spectrometers, liquid chromatographs, viscosimeters, densimeters, blood test equipment, urinalysis equipment, storage and the like.

BACKGROUND OF THE INVENTION

As disclosed in U.S. Pat. No. 7,824,613, the disclosure of which is incorporated herein by reference, there are many situations where large number of analytical instruments are used to conduct large numbers of chemical, physical or biological tests on liquids. Examples of such laboratories are oil refineries, chemical plants, pharmaceutical manufacturing operations, forensic laboratories, medical laboratories, food manufacturing operations and the like.

Typically, a sample is taken at a location outside the laboratory delivered to a sample preparation station where an individual, machine or robot withdraws a suitably sized portion and places it in a clean specialized container known as a vial. Records are made to indicate when and where the sample was taken and suitable information is placed on the sample container so results can be appropriately correlated for study and analysis.

In a typical large analytical laboratory, sample vials are loaded in a tray and manually delivered from the sample preparation station to a bank of analytical instruments, of which gas chromatographs (GCs) or combinations of gas chromatographs, liquid chromatographs and mass spectrometers (MSs) are common. An individual loads the vials into the inlet tray or autoloader of the GCs or MSs and the analytical instruments more-or-less operate automatically to conduct the programmed tests on the samples in the vials, generate reports and transport the vials to an output tray of the instrument where the vials are ultimately collected and either discarded or temporarily stored.

Disclosures of some interest relative to this invention are found in U.S. Pat. Nos. 1,733,026; 4,941,777; 4,886,401; 5,234,292; 5,337,920; 5,441,699; 5,623,415; 5,682,026; 5,805,454; 6,071,477; 6,128,549; 6,141,602; 6,659,693; 6,974,294, 7,407,627 and 7,824,613 and U.S. printed patent publications 2002/0198738, 2004/0100415 and 2006/0120835.

SUMMARY OF THE INVENTION

As disclosed herein, one of the problems with prior art laboratories is the inability to store sample vials in such a way that they are easily retrievable and are secure against many or all human errors. A disclosed technique for storing large numbers of vials is to provide a number of containers or cartridges which can be stored in a suitable location and then installed in a device where the vials are retrieved. The containers can comprise one or more discs each of which has a large number of recesses to receive sample vials. In a multiple disc device, vials from discs below the top disc are retrieved by providing through passages in the superposed discs, rotating the discs so that the passages align with the vial selected to be removed and then passing the vial through the superposed disc or discs into a conveyor system which transports the vial to a desired location, such as an analytical instrument, a sample distribution station, a sample identification station, a long term storage device or other location.

Transport of the vial may preferably be done by use of a venturi like device to produce a low pressure adjacent the vial to lift or pull the vial from its rest location into a conduit and to produce a high pressure area to push the vial from the venturi like device to a desired location. One problem with transporting vials by a venturi like device feeding into a conduit is the vials have an aggravating tendency to spin rather than be propelled along the conduit. This is because the vials do not have a seal on the exterior mating with the conduit wall, i.e. the vials are propelled by creation of a pressure drop across the vial caused by air flowing around the vial.

As disclosed in U.S. Pat. No. 7,824,613, vials are transported along one of a series of conduits leading to one of a series of analytical instruments, i.e. each instrument has a different conduit leading to it. It has been discovered that the number of conduits can be drastically reduced by incorporating a switch or diverter in a common conduit to direct sample vials to any one of a multiplicity of instruments.

It is an object of this invention to provide an improved system for transporting sample containers to and/or from a bank of analytical instruments.

A further object of this invention is to provide an improved storage system for large numbers of sample containers.

A more specific object of this invention is to provide a venturi like device for withdrawing sample vials from a container and propelling them along a conduit.

A further object of this invention is to pneumatically transport vials through a conduit and preventing spinning of the vial.

Another object of this invention is to provide an improved technique for plumbing conduits leading to a large number of analytical instruments.

Another object of this invention is to provide a simplified system incorporating a vault in which vials may be securely stowed.

These and other objects and advantages of this invention will become more apparent as this description proceeds, reference being made to the accompanying drawings and appended claims.

BRIEF DESCRIPTION OF THE DRAWINGS

FIG. 1 is a partly schematic, partly pictorial view of a vial handling system;

FIG. 2 is an exploded isometric view of a sample vial and a recess in a sample disc, part of which is broken away for clarity of illustration;

FIG. 3 is an enlarged isometric view of a vial storage cartridge, certain parts being broken away for clarity of illustration;

FIG. 4 is a side elevational view of a vial storage vault having a cartridge of FIG. 3 therein, certain parts being broken away for clarity of illustration, showing a vial being pulled upwardly out of a vial cartridge;

FIG. 5 is a view similar to FIG. 4 showing a vial being delivered through the cartridge to a conduit;

FIG. 6 is a top view of one of the storage discs inside the vial storage cartridges of FIGS. 4-5;

FIG. 7 is an enlarged side elevational view of a bank used to receive a removable tray of vials and direct the vials to desired locations;

FIG. 8 is a side elevational view of another vial reversing mechanism;

FIG. 9 is an exploded view, partly in section, illustrating one of the venturi devices and part of the downstream conduit;

FIG. 10 is a side view, partly in section, of a router used in the vial handling system of FIG. 1;

FIG. 11 is a side view, partly in section, of a vial diverter used in the vial handling system of FIG. 1;

FIG. 12 is an enlarged view of one of the analytical instruments in the system of FIG. 1;

FIG. 13 is a schematic view of a simplified system;

FIG. 14 is a top view of a system input/output station;

FIG. 15 is a partial cross sectional view of FIG. 14, taken along line 15-15 thereof as viewed in the direction indicated by the arrows;

FIG. 16 is a top view of a vault having a storage cartridge nested therein, panels of the vault and storage cartridge being omitted for illustrative purposes;

FIG. 17 is a side view of the inside of the vault showing a pair of arms having mechanisms thereon for manipulating sample vials, part of the storage disc being broken away for illustrative purposes;

FIG. 21 is a broken view of a storage disc and brake assembly showing the storage disc braked to prevent rotation; and FIG. 22 is a view similar to FIG. 21 showing the brake released to allow rotation of the storage disc.

DETAILED DESCRIPTION

Figure 18:
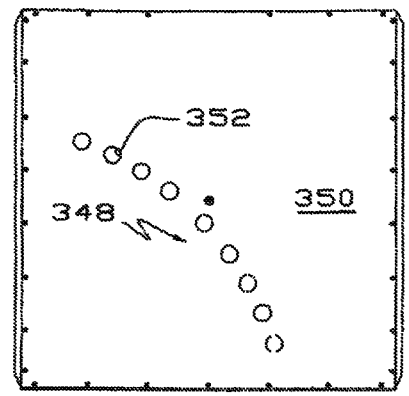
FIG. 18 is a top view of the storage cartridge of FIG. 16.

Referring to FIGS. 1-7, there is illustrated a system 10 for handling a large number of sample containers or vials 12 in an analytical laboratory 14 having a large number of analytical instruments 16 such as gas chromatographs, mass spectrometers, viscosimeters, densimeters, blood test equipment, urinalysis equipment and the like which have heretofore been operated singly rather than as a bank of interrelated instruments. For purposes of convenience, the system 10 will be described in conjunction with a bank of GCs, it being understood that the system is equally useful with a bank of other analytical instruments or a bank of mixed analytical instruments. It will also be understood that the bank of analytical instruments may include instruments not controlled, or only partially controlled, by the system 10.

A typical analytical laboratory 14 may include a bank of GCs 16 having a conventional autoinjector 18 which receives the conventional vial 12 having a septum 20 in a screw on lid 22 so a sample of the liquid in the vial 12 may be withdrawn by a sampling needle (not shown) in the autoinjector 18, as is conventional in modern GCs. It will be understood that other modern analytical instruments have similar automatic injectors for processing a sample vial after it reaches the instrument.

One of the problems in some types of laboratories, of which forensic labs are an example, is the requirement to house large numbers of vials 12 in a secure manner, while providing access to them in a simple, expeditious manner. A series of cartridges 24 may be provided to hold a substantial number of vials 12. A large number of the cartridges 24 may be stored on suitable racks 25 in temperature controlled rooms or other suitable locations. The cartridge 24 includes a housing 26 and may have a read/write storage device 28 therein accessible through a conventional electronic connector 30 for recording and/or retrieving information about the location of the vials 12 in the cartridge 24 and/or the contents of samples in each of the vials 12. Each cartridge 24 is identified in any suitable manner, as by indicia 32, so it can be retrieved from its storage location. The information recorded in the storage device 28 may differ, depending on the type laboratory in which the cartridge 24 is being used, but may preferably include the date the sample was taken, the location were it was taken, the individual who retrieved the sample from its previous location, identifying information about the case or proceeding that the sample relates to and the like. One or more suitable handles 34 may also be provided.

In some applications, the cartridges 24 are intended for moderate-to-long term storage. In these situations, the housing 26 may preferably be made so that when the vials 12 are loaded into the cartridge, the information about the samples are recorded on the storage device 28. Inside the housing 26 may be a series of superposed discs 36 having a large number of recesses 38 arranged in circular rows having an opening 40 in the bottom wall 42 for purposes more fully apparent hereinafter. Although the size of the recesses 38 may vary substantially, it is preferred that they be only slightly larger than the outer diameter of the vials 12 and only slightly deeper than the height of the vials 12. In this or other suitable manner, the vials 12 remain in their recesses 38 during normal handling of the cartridge 24. In the illustrated embodiment, there are three such discs 36 but it will be understood that there may be any suitable number. Each of the circular rows includes at least one through passage 44 for purposes more fully apparent hereinafter. The cartridge housing 26 may be designed in any suitable manner to retain the vials in their recesses 34 while providing access to them. One convenient way to provide access is for a top wall 46 to provide a series of openings 47 or an elongate slot therein sized so the vials 12 may be withdrawn through the top wall 46 as explained hereinafter.

When it is time to retrieve one of the vials 12 from the cartridge 24, the cartridge 24 is removed from its storage location and placed in a retrieval device or vault 48. The vault 48 may comprise a rectangular sleeve or docking station 50 having an opening or through passage sized to receive the cartridge 24 and provides access to the electronic connector 30 communicating with the storage device 28 so its information may be read by a computer (not shown) to decipher and display the stored information and to provide information about the location of a desired vial. The top wall 52 of the vault 48 may also include a series of openings 53 spaced to align with the openings 47 when a cartridge 24 is located in the vault 48. To this end, the vault 48 may include some mechanism to position cartridges therein at a consistent, repeatable location. In some embodiments, a slot (not shown) may be incorporated into the top wall 52 of the vault 48 in lieu of the openings 47. In any event, as shown in FIGS. 3-4, a pick up device 54 is movable along the path of the openings 47 to withdraw a vial 12 from its recess 38 in a manner disclosed hereinafter. The pick up device 54 may be mounted on a suitable support 56 for movement above the aligned openings 47, 53 in response to signals to a motor (not shown) in a manner analogous to an x-y positioner. The pick up device 54 is capable of picking up a vial from its recess 38 in any of the superposed discs 36. It will be seen that each of the recesses 38 has a unique addressable location.

The discs 36 are mounted for independent rotation about a common axis 58 in any suitable manner, as by mounting the discs 36 on a common bearing-spindle assembly 59, by the provision of gear teeth 60 on the periphery of the discs 36 and a series of independently motor driven gears 62 inside the vault 42. In some embodiments, it will be seen that vials 12 in the upper disc may be retrieved in a straight forward manner because the pick up device 54 may be positioned immediately above any of the openings 53 in the vault 48 and the discs 36 can be rotated to any angular position so any vial recess in any of the circular rows of the upper disc can be accessed by the pick up device 54.

By a comparison of FIGS. 3-6, it will be seen that correct rotation of the uppermost disc aligns each vial recess 38 with the openings 47, 53 so any vial 12 in the outermost row of the middle disc by suctioning it through the passages 47, 53.

To retrieve a vial in the outer row of the middle disc, the through passage 44 of the upper disc is aligned under the passages 47, 53 and the middle disc is rotated so the recess 38 of the desired vial is aligned with the passages 47, 53 and the pick up device 54 so the pick up device 54 can withdraw the desired vial. If a vial in one of the other rows is desired to be retrieved, the upper disc is rotated so the through passage 44 in the desired row aligns with the passages 47, 53 so the pick up device 54 can retrieve a vial from the desired row.

Similarly, the pick up device 54 can retrieve vials from the lowermost disc 36 by aligning the through passages 44 in the upper and middle disc with the passages 47, 53 and rotating the lowermost disc so the desired recess aligns with the passages 47, 53. Thus, the pick up device 54 can pick up any vial 12 in the lower disc. It will thus be seen that by correcting positioning the discs 36, the pick up device 54 is able to retrieve any vial 12 from any of the recesses 38 in any of the discs 36. Thus, FIG. 4 shows a vial being pulled upwardly from the lower disc 36 through the middle and upper discs 36 into the pick up device 54.

Although the discs 36 are circular and rotate to position the passages 44 and vial recesses 38 appropriately, it is possible to make the discs 36 square or rectangular and move one or more of them to align passages 44 and recesses 38 to retrieve or delivery vials from or to a subjacent disc. The housing 26 may preferably be closed and secured in some convenient manner and the discs 36 may be positioned so none of the vials are able to move or fall out of the cartridge 24 regardless of the orientation of the cartridge 24. This may be accomplished in any number of ways, e.g. aligning all of the passages 44, 47 and then applying a brake to each of the discs 36, misaligning the recesses 38 and the passages 47 and applying a brake to each of the discs 36 or any other suitable means. As explained more fully in connection with FIG. 16, the brake may be of any suitable type.

There are several ways to deliver the vials 12 from the pick up device 54, i.e. send them upwardly from the pick up device 54 to a desired location, send them downwardly through the discs 36 to a desired location or move them laterally to a transportation device. Sending them upwardly has the disadvantage of having to provide a flexible conduit capable of accommodating movement of the pick up device 54, so it may be preferred to deliver them downwardly through the discs 36 to a venturi 64 sending the vial through an outlet conduit 66. If the vials 12 are being delivered upwardly from the pick up device 54, there is no need to have through passages 44 in the lowermost disc but when delivering the vials 12 downwardly through the discs 36 to the outlet conduit 66, at least one through passage 44 in each row of recesses 38 in the lower disc 32 allows the vials 12 to pass into the conduit 66. Thus, FIG. 5 shows the vial being dropped through the discs 36 into the venturi 64 which provides the motive power to transport the vial 12 to a desired location. It will accordingly be seen that the through passages 44 in the discs 36 allow movement of the vials 12 upwardly and downwardly through the cartridge 24. It will be understood that with only one outlet conduit 66, only one through passage 44 may be provided in the lowermost disc 32. However, it may be preferred that all of the discs 36 are identical or it may be preferred to deliver vials 12 from different through passages 44 to different desired locations.

There are a variety of techniques by which the vials 12 may be withdrawn from the discs 36 and sent to a bank 70 or other desired location. A suitable technique is to use a device, such as a venturi, producing a low pressure area to suction any desired vial 12 out of its recess 36. To this end, the opening 40 in the bottom wall 42 of each recess 36 allows air from inside the cartridge 24 to flow upwardly through the recess 36 where the selected vial 12 is located thereby propelling the vial upwardly in response to operation of a venturi type pick up device 54.

Typically, vials 12 from the vault 48 are delivered to a bank 70 where a computer (not shown) and necessary controls (not shown) determine the route and destination of the vials 12, i.e. to a selected instrument 16 or other desired location. It will be understood, of course, that this routing control may be built into the vault 48, if desired, rather than the bank 70. The bank 70 may be preferred because many, if not most, of the vials 12 that are to be analyzed are not stored in the medium-to-long term storage afforded by the cartridges 24 and vault 48. The bank 70 accordingly accommodates a removable tray 72 having vial receiving recesses similar to the recesses 36 for retaining vials 12 to be analyzed. The tray 72 may be rectilinear so a pick up device 74 is mounted on an x-y positioner 76 for movement above the tray 72 to pick vials 12 up out of the tray 72. It may be desirable, in some embodiments, that the pick up device 74 is directly attached to an upwardly extending flexible conduit to send vials 12 directly to the instruments 16. In the device disclosed, however, the pick up device 74 drops the vials 12 into a passage 78 for delivery to the instruments 16 for reasons discussed shortly.

When the vials 12 are delivered from the bank 70, there are times when it may be desirable to deliver them head first, i.e. with the lid 22 down, or feet first, i.e. with the lid 22 up. The vials 12 may preferably be loaded in the removable tray 72 head up, i.e. with the lid 22 up, so when they are dropped into the passage 78 in the position shown in FIG. 7, the vials 12 pass feet first through a conduit 80 having a venturi 82 therein and are transported toward the instruments 16 or other desired location. It will be seen that the conduit 80 delivers the vials 12 to the instruments 16 feet first, i.e. lid 22 up, which may be the desired orientation for operation of the auto-injectors 18 of the instruments 16. In other words, the conduit 80 does not reverse the orientation of the vials 12.

It may be desirable to have some mechanism to reverse the orientation of the vials 12, i.e. deliver them head first to a desired location. It may be desirable to have an orientation reversing mechanism used in conjunction with the bank 70 to send vials head first to a storage device such as the cartridge 24 in order to load vials from the bottom, to another bank (not shown) analogous to the bank 70 or mounted in association with the vault 48 to send vials head first to the bank 70. To this end, a vial reversing device 84 includes a conduit having a Y or V shaped section 86 including conduit sections 88, 90 arranged at an angle 92 therebetween. The conduit section 88 connects through a conduit 94 to a passage (not shown) provided behind the passage 78 in FIG. 7 so the x-y positioner 74 can drop the vial into either the passage 78 or the second passage behind it.

In the embodiment of FIG. 7, a vial falls by gravity or is pulled by a venturi 96 into the bight or junction 98, between the conduit sections 88, 90, that is of a sufficient length to receive the vial 12. When the vial 12 arrives at the junction 98, its presence is detected by a sensor 100, such as a photocell. Suction of the venturi 96 is released so the lid end of the vial 12 falls slightly to align with the conduit section 90. The venturi 96 either pushes the vial 12 toward the conduit section 90 or a venturi 102 pulls the vial 12 to the right in FIG. 7 through a conduit 104 connected to the conduit section 90. A venturi 102 accordingly delivers the vial 12 in an opposite orientation to a desired location for the vial 12, such as through the conduit 66 to the vault 48. It will be apparent that a computer (not shown) choreographs operation of the pick up device 74, the x-y positioner 76 and the venturis 96, 102 to accomplish reversing the orientation of the vials 12 as they pass through the reversing device 84.

It may be preferred that the reversing device 84 be bidirectional, i.e. it will reverse vials leaving or approaching the bank 70 or any other component on which the reversing device 84 is mounted. In these embodiments, it may be preferred to make the angle 92 an acute angle which facilitates bidirectional operation because the vial 12 can more easily be tipped from head up to head down and vice versa, in the case of a gravity assisted device or moved from head left to head right in the case of a venturi assisted device.

It will be apparent that other embodiments of the reversing mechanism are equally operable. One such reversing mechanism 108 is illustrated in FIG. 8 and comprises a Y or V shaped conduit 110 including first conduit 112 joining a second conduit 114 at a junction or bight 116 that is sufficiently long to receive the vial 12. A sensor 118 at or near the junction 116 detects the presence of a vial 12 and starts operation of a venturi 120. In the reversing mechanism 108, the vial 12 falls by gravity into the junction 116, meaning that the inlet to the conduit 112 is sufficiently above the junction 116 so the device works reliably. In the embodiment of FIG. 7, there is no such requirement because the venturi 96 may pull the vial 12 into the junction 98. The reversing device 108 may be located at any desired location where reversing the vial may be necessary or desirable and may be used in conjunction with a non-reversing conduit 122 and venturi 124 for delivering vials in the opposite orientation.

Referring to FIG. 9, there is illustrated a venturi 126, which may act as the pick up device 54 in the vault 48, as a pick up device 74 in the bank 70, as a propulsion device in the vial reversing mechanism 84, as a vial propulsion device in the system 10 and the like. The venturi 126 includes a base 128 having an threaded inlet passage 130 and a threaded power fluid inlet 132 connected to a conduit 134 having a valve 136 therein controlled by an operator, which may be a human, machine or robot, 138 in response to a signal over a wire 140 or other communication link. The conduit 134 connects to a source of compressed gas, which in most situations is air, but which in some situations may be some inert gas such as nitrogen. Operation of the valve 136 is controlled by signals over the communication link 140 by a computer (not shown) which operates the valve 136 at appropriate times.

A power unit 142 includes a body 144 having threads 146 to mate with the threaded passage 130 which may be sufficiently long to connect to a female coupling 148 on an inlet conduit 150. The power unit 142 may also include a central passage 152 and a series of symmetrically placed inclined passages 154 angled relative to a flow axis 156. The inclined passages 154 communicate between the central passage 152 and the exterior of the body 144. The power unit 142 includes a nut 158 and threads 160 at an end opposite from the threads 146 to connect the power unit 142 to a female connection 162 on a flow conduit 164. A gasket or seal 166 is captivated between the nut 158 and the base 128 to create a pressure compartment 168 open to the angled passages 154.

Operation of the venturi 126 will be seen to be conventional, producing a flow in the venturi 126 along the axis 156 and a low pressure area adjacent the conduit 150 which is sufficient to pick up vials 12 out of the recesses 38 in the cartridge 24, out of recesses in the tray 72, to pull vials into the reversing mechanism 86 and to propel vials 12 through the system 10.

One problem associated with transporting vials 12 pneumatically is a tendency of the vials 12 to spin about their longitudinal axis 170 at a fixed location rather than be propelled along the conduit 164. It will be recognized that the vials 12 do not have a gasket on their exterior to seal against the inside of a conduit so a vial 12 is propelled by a pressure differential across the vial caused by the propulsion gas flowing around it. This tendency of the vial 12 to spin, rather than be propelled along the conduit 164, was discovered to be related to the amount of propulsion gas passing through the conduit and the technique used to bleed off some of the propulsion gas. Without being bound by any theory, it appears that transport of the vials can be accomplished at a relatively low pressure drop across the vial but at a higher pressure drop, the vials spin without moving along a path of desired transport inside a conduit.

It was ultimately recognized there was an excessive amount of gas, in most situations the gas being air, propelling the vial through the conduit 164. It was recognized that the amount of propulsion gas flowing through the conduit 164 was the sum of the power gas injected through the power fluid port 132 and air flowing upwardly through the nipple 150. In order to reduce the amount of gas and thereby reduce the velocity of the vials passing through the conduit 164, it may be preferred to bleed some of the gas off downstream of the venturi 126. To this end, the conduit 164 or an extension of the power unit 142 may be provided with bleed off ports 172. It was discovered that spinning of the vials 12 did not cease until the ports 172 were symmetrically arranged. Without being bound by any theory, it appears an unsymmetrical arrangement of bleed off ports 172 causes a swirling motion of gas inside the conduit 164 which precipitates spinning of the vial 12. Thus, the bleed off ports 172 may be of any suitable number and may preferably be symmetrically arranged about the axis 156 of the conduit 164. The cross-sectional area of the bleed off ports 172 may preferably be in the range of 40-60% of the cross-sectional area of the low pressure inlet provided by the nipple 150 and may ideally be about fifty percent of the cross-sectional area.

Referring to FIGS. 1 and 10, a conduit 174 connects the bank 70 with a router 176 which may direct the vials 12 either to a bank of GCs 16, a vault 178 comparable to the vault 48 or other suitable destination. The router 176 may be of any suitable type and is illustrated as comprising a base 180 having a series of outlet ports 182 from which extends a conduit 184 leading to the vault 178 and a series of conduits 186, 188 leading to the GCs 16. A member or car 190 is guided by the base 180 for linear movement along a path above the ports 182 in response to a force applier 192 such as a worm screw rotated by a motor 194. The member 190 includes a fitting 192 connected to a flexible end of the conduit 174 so the conduit 174 is selectively aligned with any of the ports 182 to thereby deliver a vial to any of the conduits exiting from the router 176. It will be appreciated that there may be some air leakage between the car 190 and the ports 182 which can be offset by supplying sufficient compressed gas to propel the vials 12 to their desired locations.

It will be appreciated that operation of the motor 194 is under control of a computer (not shown) that dictates movement of a particular vial to a particular location. Suitable means may preferably be provided to ensure reliable operation of the router 176. To this end, a sensor 200 may be provided to detect passage of a vial through the router 176. The sensor 200 connects to a communication link 202 leading to the control computer. Suitable means may preferably be provided to insure that the car 190 is in its intended position, such as an energy source or other position locator (not shown) adjacent each of the ports 182 and a suitable sensor on the car 190 to detect the appropriate locator.

In the illustrated embodiment of FIG. 1, the router 176 may direct vials either to or from the vault 178 or may direct vials to or from a bank of the GCs 16. In U.S. Pat. No. 7,284,613, a conduit was provided leading to each of the analytical instruments 16. It has been realized that a preferred technique may be to provide fewer conduits in order to simplify installation. As illustrated in FIG. 1, it may be preferred to have only two conduits 186, 188 leading to the GCs, one for delivering vials toward the GCs and one for retrieving vials from the GCs. In some low traffic embodiments, only one conduit is needed and vials may be delivered and retrieved in the same conduit in much the same manner as trains, with proper scheduling, can travel in opposite directions on a single track.

Near each of the GCs is a switch or diverter 204 that has the capability of diverting a vial to the adjacent GC or sending the vial down the line toward one or more downstream GCs. To this end, as shown best in FIG. 11, the diverter 204 may comprise a housing 205 where the conduits 186, 188 are connected to a housing wall. Communicating with the conduits 186, 188 are flexible conduits 206, 208 which terminate in a fitting 210, 212 fixed, as by threads 214, 216 or the like, to a shiftable plate 218. The plate 218 slides on a second plate 220 and may be moved in any suitable manner, such as by a suitable motor 222 rotating a screw 224 to position the plate 218 so the conduits 206, 208 connect either to a first set of ports 226, 228 or to a second set of ports 230, 232.

The first set of ports 226, 228 connect to conduits 234, 236 leading to the GC 16. The GC 16 is illustrated as a two channel gas chromatograph having two autoinjectors and two operating mechanisms, i.e. it is basically two GCs in one. Thus, the diverter 204 is arranged to accommodate a single two channel GC or two adjacent single channel GCs. It will be understood, of course, that the diverter 204 may be configured to accommodate other situations such as one single channel GC or several multiple channel GCs.

A second set of conduits 238, 240 connect to the first diverter 204 and act to send vials downstream toward another suitable location, such as the downstream GCs on the right of FIG. 1 and to pass vials from the downstream instruments back toward the router 176.

Referring to FIG. 12, there is an enlarged view of the GC 16 illustrating the conduits 234, 236 each terminating in a venturi 242 controlled by an instrument controller 244 which is, in turn, controlled by a computer (not shown) operating the system 10. The venturi 242 receives a vial 12 through the conduit 234 and slows it down by delivering a puff of air upwardly into the conduit 234 in response to instructions from the system computer (not shown) as instigated by a signal from a sensor or sensors 246 on the diverter 204 detecting the approach of a vial. The conduit section 248 of the venturi 242 is positioned directly over a turret 250 of the auto-injector 18 so the vial is delivered to the turret 250 and the GC acts on the vial to remove a liquid sample and conduct its prescribed analysis. When the GC is finished with the vial 12, the turret 250 returns the vial to a position immediately below the conduit section 248. In response to a signal from the system computer as initiated by a sensor (not shown) in the turret 250 or conduit 248, the venturi 242 suctions the vial into the conduit 234 and propels it toward the nearby diverter 204. The systems computer indexes the plate 218 of the diverter 204 so the vial passes into the conduit leading toward the bank 70. Before the vial arrives at the router 176, a signal from the systems computer shifts the car 190 to a position so the vial enters the conduit 174 and passes into the conduit 80 (FIG. 7) and appears at the opening 78. The x-y positioner 76 picks the vial out of the opening 78 and either drops it in its prescribed recess in the tray 72 or delivers it through the reversing device 84 to the vault 48.

It is apparent that a computer (not shown) choreographs operation of the vault 48, the bank 70, the router 176, the bank 178 and the switches 204 to accomplish delivering and retrieving vials 12 to and from the instruments 16.

Referring to FIGS. 13-20, there is illustrated a somewhat different system 300 for handling a large number of sample containers or vials 12 in an analytical laboratory having a large number of analytical instruments 302 such as gas chromatographs, mass spectrometers, viscosimeters, densimeters, blood test equipment, urinalysis equipment and the like which have heretofore been operated singly rather than as a bank of interrelated instruments. The system 300 may include, as major components, an input/output station 304, a router 306, one or more pairs of conduits 308, 310, and a vault 312 having a storage cartridge or container 314 therein. The router 306 directs vials between the instruments 302, station 304 and vault 312. It will be recognized that, as illustrated, one of the conduits 308, 310 delivers vials toward the instruments 302 and the other of the conduits 308, 310 delivers vials from the instruments. In some low traffic embodiments, only one conduit is needed and vials may be delivered and retrieved in the same conduit in much the same manner as trains, with proper scheduling, can travel in opposite directions on a single track.

The input station 304 may be of the x-y positioner type shown in FIG. 7 or may preferably be of a radial type shown in FIGS. 13-15. The station 304 may include a stationary base 316 and a base 318 that is rotatable about an axis 320 and indexed by a suitable motor (not shown). The base 318 includes a circular array of recesses 322 for holding a number of vials 12. The user may swipe the vial 12 past a reader/encoder 324 to read a machine readable tag or indicia on the vial and encode identifying information about the vial 12 so this information can be stored in memory in the storage cartridge along with the position of the recess 322 into which it is put. An assembly 326 may be provided to retrieve vials from any particular recess 322 and accordingly may include a venturi device 328 providing a low pressure region pulling a vial out of its recess 322 and delivering it to a conduit 330 leading to the router 306.

The router 306 may be of any suitable type and is illustrated in FIG. 13 as of a linear type having a stationary base 332 from which extend the conduits 308, 310, the conduit 330 leading to the input/output station 304 and one or more additional conduits 334 leading to another router, another vault, another input/output station or other desirable location. It will be seen that the system 300 is designed for the input/output station 304 to deliver vials only to, and receive vials only from, the vault 312 as opposed to sending vials from the input\output station 304 directly to the instruments 16. The purpose of this is to reduce human errors caused by faulty or inaccurate encoding of vial information. Delivering vials only to the vault 312 may be accomplished by hardware in the sense there is only one path of entry into the storage cartridge 314 or may be accomplished by software, i.e. providing instructions that can only deliver vials through the entry/exit array 348. The router 306 also includes a linearly slidable connection 336 including a vial approach sensor (not shown) mounted for movement past the conduits 308, 310, 330, 334 so a motor 338 can be controlled to deliver vials in desired directions.

When delivering vials to and returning vials from the instruments 302 through the conduits 308, 310, a switch or diverter 340 can be provided adjacent each instrument 302 or at any location where it is desired to change the direction of travel of the vial. The diverter 340 has at least two, and may preferably have only two positions, i.e. one position allowing vial travel past the assembly and one position diverting the valve to or from the adjacent instrument 302. To this end, each diverter 340 can be of the same type as the diverter 204 shown in FIG. 11. The diverter 340 is illustrated as including a shiftable plate 342 sliding on a second plate 344 and may be moved in any suitable manner, such as by a rack and pinion arrangement 346 so vials can be sent either to or from the adjacent instrument 302 or sent past the adjacent instrument 302 to a downstream instrument.

The vault 312 and storage cartridge 314 are best shown in FIGS. 16-20. The storage cartridge 314 may include a receptacle that is closed except for an entry/exit array 348 in a top wall 350 which may comprise a slot or a series of openings 352 in an arc and a similar array 354 in a bottom wall 356 which may comprise a series of openings 358. The openings 352 are of a size to pass the vials 12 but the openings 358 are too small to pass the vials 12 for purposes more fully apparent hereinafter. Regardless of whether the receptacle is closed, the top and bottom walls 350, 356 are such that there is no opening of a size that will pass the vials 12. This in conjunction with the operation of the mechanism to load and unload the storage cartridge gives considerable confidence that the position of any particular vial is known as explained more fully hereinafter. In other words, the only path or paths where a vial 12 can be added to or retrieved from the disc 360 is through the entry/exit array 348.

The storage cartridge 314 may include a single storage disc 360 having a large number of recesses 362 which can be arranged in circular rows or other suitable arrangement. The recesses 362 are of slightly different configuration than the recesses 38 to accommodate vials of different configuration. The disc 360 may be mounted for rotation on a bearing-spindle assembly 364 and includes a force receiving drive connection which may be a circular array of gear teeth 366 on a circumference of the disc 360, such as on an edge of the disc. As shown schematically in FIG. 16 and more completely in FIGS. 21 and 22, a brake 368 may be provided to prevent the disc 360 from accidently rotating as more fully apparent hereinafter. To this end, a gear segment 370 may be provided having a complementary curvature to the gear provided by the teeth 366. A spring 371 can bias the gear segment 370 into normal braking relation with the gear teeth 366 and a mechanism 372 may be provided to retract the gear segment 370 when the storage cartridge 314 docks in the vault 312.

To this end, the mechanism 372 can be mechanical in nature as shown in FIGS. 21-22 and can comprise a lever 373 connected by a flexible link 374 to the gear segment 370 and having sufficient mechanical advantage to tension the spring 371 and thereby release the brake provided by the gear segment 370. The gear segment 370 can be slidably mounted on a support 375 for movement toward and away from the storage disc 360 so that tension in the spring 371 moves the gear segment 370 into braking engagement with the gear teeth 366 in a normal relaxed position of the lever 373.

The mechanism 372 can be actuated by a solenoid plunger 376 of a solenoid 379 carried by the vault 312. When the cartridge 314 is inserted into a docking station provided by the vault 312, operation of the vault 312 can begin in response to a security device 377 such as a biometric sensor of any suitable type, such as a fingerprint device or iris camera. Thus, the solenoid plunger 376 can advance through an opening 378 (FIG. 20) in the bottom cartridge wall 356 to engage and move the lever 373. The solenoid plunger 376 accordingly has two functions because it latches the cartridge 314 in place in the vault 312 and also trips the lever 373 to retract the braking gear segment 370. Because of the biometric sensor in the security device 377 operation of the vault 312 by unauthorized personnel is minimized. Similarly, the security device 377 can be incorporated into a procedure to retract the solenoid plunger 376 and remove the cartridge 314 thereby minimizing the opportunity for authorized personnel to remove cartridges 314 from the vault 312.

The storage cartridge 314 may also include a memory device 380 for storing information about the contents, source and location of each of the vials 12 inside the storage cartridge 314. In the alternative, the storage cartridge 314 may include a memory device for storing a set of characters identifying the particular cartridge 314 so data about the contents, source and location the each of the vials 12 may be recorded in a remote storage device, such as a server. In any event, some means are provided in the cartridge to allow retrieval of information concerning the identity of each of the vials 12 and their location.

The storage cartridge 314 may also include a reader 382 recognizing markings on the edge of the disc 360. In some embodiments, a zero marker is used to return the disc 360 to a home position when the storage cartridge 314 is ready to be removed from the vault 312 or at the end of any operation retrieving or adding a vial to the storage cartridge 314 thereby avoiding cumulative rotational errors caused by gear lash or the like. It will be seen that the reader 382 is used to orient the disc 360 when it is desired to retrieve a vial 12 from the disc 360 or to add a vial 12 at a specific location on the disc 360.

The storage cartridge 314 is accordingly removably received in a docking station inside the vault 312 and can be removed and replaced at will to provide a very large storage capacity, depending only on the number of discs 360 in each storage cartridge and the number of storage cartridges 314 in use.

Referring to FIGS. 16 and 17, the vault 312 may comprise any suitable means for retrieving vials from the disc 360 or adding vials to the disc 360 but a preferred approach is pneumatic, either vacuum, pressure or a combination of vacuum and pressure. There is accordingly a conduit 384 (FIG. 13) leading from the shiftable connection 336 on the router 306 to the vault 312 that terminates in a connection 386 that opens upwardly. The connection 386 is accordingly a site or vial transfer station where vials are transferred to and from the storage cartridge 314. Incoming vials 12 stop in the connection 386 and are picked up by an arm 388 and deposited in one of the many recesses 362 of the disc 360. Outgoing vials 12 are picked up from one of the recesses 362 by the arm 388 and deposited into the connection 386.

To these ends, the arm 388 is above the disc 360 and a lower arm 390 may be provided below the disc 360 for purposes more fully apparent hereinafter. The arms 388, 390 may be mounted on a common shaft 392 for pivotal movement about a common axis 394. The shaft 392 is rotated by a motor 396 as controlled by a control system 398. The arms 388, 390 may accordingly be mounted for arcuate movement between the connection 386 and any one of the openings 352 comprising the entry/exit array 348. One of the functions of the vault 312 is to encode information from the vials 12 and store the information in memory 380 and in memory in the control system 398. To this end, a reader 400 may be provided adjacent the connection 386. When the arm 388 picks up a vial from the connection 386 and/or when the arm 388 deposits a vial in the connection 386, it may place the vial 12 adjacent the reader 400 so vial information can be read and stored. It may accordingly be preferred that any vial 12 entering and/or leaving the storage cartridge 314 is passed adjacent the reader 400 so the information of the location of the vial 12 can be recorded.

The mechanism by which the vials 12 are retrieved from the recesses 362 or picked up from the connection 386 may vary widely. Accordingly, the arm 388 may include a venturi vacuuming the vials upwardly or the arm 390 may provide a source of air 402' delivering a puff of air through the selected opening 358 in the bottom wall 356 of the storage cartridge 314 thereby pushing a selected vial upwardly into a receptacle 402 against a spring stop 406. A sensor 408 may detect the presence of a vial in the receptacle 404 and actuate a solenoid 410 to push a rubber tipped probe 412 through an opening in the receptacle 402 against the vial 12 and thereby pin the vial in the receptacle 402. The arm 388 is then rotated to overlie the connection 386 and the solenoid 410 is deactivated to drop the vial 12 by gravity into the connection 386. Delivery of the vial into the connection 386 is detected by a sensor 414 to activate a venturi 416 to deliver the vial to the router connection 336 and then along one of the conduits 308, 310, 330, 334 toward its desired location. It will be seen that the arm 388 picks up vials from the connection 386 in the same manner as from the recesses 362, i.e. the arm 388 is positioned over the connection 386 so a vial is delivered upwardly into the receptacle 402, detected by the sensor 408, pinned by the solenoid actuated tip 412 and then swung to its selected position above one of the entry/exit openings 352 and dropped into position.

In the illustrated configuration where the arms 388, 390 are fixed to the same shaft 392, there is a mechanical interference problem with the lower arm 390. The conduit 384 terminates in the connection 386 and contacts the arm 390 in an attempt to place the arm 388 overlying the conduit 384 and reaching the reader 400. To overcome this, the arm 390 may be pivoted intermediate the ends thereof, as at a pivot connection 418, and a spring 420 normally biases the arm 390 into a normal position. Thus, when the arm 388 is swung to a position over the connection 386, the arm 390 strikes the conduit 384 and the pivot connection opens allowing continued movement of the arm 388 to the connection 386 and then further to overlie the reader 400.

Figure 19:
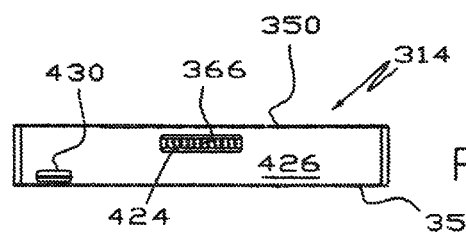
FIG. 19 is an end view of the storage cartridge of FIG. 16.
Figure 20:
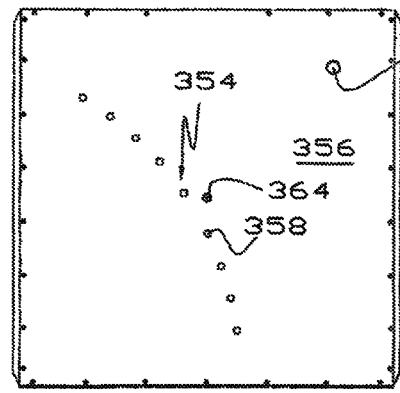
FIG. 20 is a bottom view of the storage cartridge of FIG. 16.

To position the disc 360 radially, the vault 312 includes a drive gear 422 mounted to enter a slot 424 in a rear wall 426 of the storage cartridge 314 as shown best in FIGS. 16 and 19 as the storage cartridge 314 is pushed into the docking station provided by the vault 312. Teeth 428 of the drive gear 422 mesh with the disc teeth 366 so that rotation of the drive gear 422 by a suitable motor (not shown) rotates the storage disc 360. It will accordingly be seen that rotation of the disc 360 exposes each of the recesses 362 to selected ones of the openings 352 so that each of the recesses 362 are capable of receiving sample vials 12. FIG. 19 also shows a connector 430 in the back wall 426 of the storage cartridge 314 in order to connect the control system 398 in the vault 312 to memory 380 in the storage cartridge 314.

Operation of the system 300 will now be explained. A cartridge 314 may be retrieved from a storage location and docked in the vault 312. This causes a series of operations conducted in response to the control system 398, e.g. the brake 368 is released by energizing the solenoid 379. Vials 12 are typically received at the input/output station 304 in a box or tray and are loaded by an operator, which may be a human, machine or robot, by passing the vial 12 over the reader 324 and inputting any necessary data through a data input device 432. This conditions the system 300 for further action. A monitor, printout, computer or other means instructs the operator to deposit the vial into a particular one of the recesses 322. At an appropriate time, the control system 398 and/or the operator instructs the input/output station 304 to deliver one or more particular vials 12 to the vault 312 and to a particular location on the storage disc 360 selected by the control system 398.

This causes the input/output station 304 to index to the correct location on the rotatable disc 318 so the desired vial is immediately under the venturi 328. The desired vial 12 is vacuumed up and delivered into the conduit 330. The control system 398 moves the router connection 336 to align with the conduit 330 so the selected vial 12 moves through the conduit 384 into the connection 386. The control system 398 causes the arm 388 to overlie the connection 398. The presence of a vial arriving in the connection 386 and/or in the receptacle 402 is detected by the sensors 408, 414 which activates the solenoid 410 thereby pinning the vial in the receptacle 402.

The arm 388 may then be moved by the motor 396 to overlie the reader 400 and thereby record information about the vial in memory 380 and/or in the control system 398, check the recorded data against data from memory 324 in the input/output station or the like. The arm 388 may then be moved under control of the system 398 to align with a selected one of the openings 352 in the entry/exit array 348 while the gear 422 rotates the storage disc 360 to a radial position where the desired recess 362 is immediately below the receptacle 402. The control system 398 determines when the arm 388 is correctly positioned whereupon the solenoid 410 is deenergized so the probe 412 retracts thereby dropping the vial 12 into its assigned recess 362.

When it is desired to remove one of the vials 12 from the storage disc 360, the control system 398 operates basically in reverse. The motor 422 is energized to rotate the storage disc 360 to position the desired recess 362 below the opening 352 in the entry/exit array 348 and the arms 388, 390 are swung by the motor 396 to overlie the selected opening 352. A puff of air is delivered through the source 402' to push the selected vial upwardly into the receptacle 402 whereupon the solenoid 410 is energized to push the probe 412 against the vial 12 thereby pinning it in the receptacle 402.

The arms 388, 390 are then swung toward the reader 400 so the information on the vial 12 can be verified, the arm 390 abutting the conduit 384 and pivoting to allow the arm 388 to overlie the reader 400. The arm 388 is then swung to a position over the connection 386 whereupon the solenoid 410 is deenergized by the control system 398 and the vial 12 is dropped into the connection 386. The control system 398 actuates the venturi 416 to thereby transport the vial to the router 306. The control system 398 manipulates the motor 338 thereby positioning the connection 336 to align with a selected one of the conduits 308, 310, 334 depending on the desired end location of the vial 12.

Assuming the vial 12 is being sent to one of the instruments 302, the router 306 sends the vial 12 through one of the conduits 308, 310. Assuming the vial 12 is intended to be delivered to the second instrument 302, the first diverter 340 is positioned as illustrated in FIG. 13 and the vial 12 thereby reaches the second diverter 340 which is positioned in its second position so the vial 12 passes into a turret (not shown) or other accumulation device of the instrument 302. After the instrument 302 has conducted its operation on the contents of the vial 12, the vial is delivered by a venturi or other pneumatic means into the return conduit. The control system 398 positions the diverter 340 associated with the instrument to pass the vial 12 toward the router 306 which is positioned by the motor 338 to deliver the vial 12 to the vault 312 and storage cartridge 314.

If the vial is intended to remain in storage, it is delivered into the storage container 314 with its position and other suitable information stored in memory 380 and in the control system 398. If the vial is intended to be discarded, the control system 398 actuates the vault 312 to pick the vial out of the storage cartridge and send it to the input/output station 304 where the operator can retrieve it from the rotatable base 318 in response to instructions from the control system 398 as displayed in any suitable manner.

It will be apparent that many storage cartridges 314 may be used in the system 300 thereby expanding the number of vials which can be handled or stored. To this end, the cartridge 314 may be removed and replaced by another cartridge in response to instructions from the control system 398 or from instructions input through the keypad 432. When it is desired to remove the cartridge 314 from the vault 312, the cartridge 314 is configured so none of the vials 12 can escape. This may be accomplished by the control system 398 positioning the disc 360 so the openings 352 are misaligned with the recesses 362. The control system 398 also acts to prevent the disc 360 from rotating and thereby invalidating the location information in memory 380. This may be accomplished by setting the brake 368 as by deenergizing the solenoid 379 and allowing the spring 371 to advance the gear segment 370 against the teeth 366 thereby immobilizing the disc 360.

Although this invention has been disclosed and described in its preferred forms with a certain degree of particularity, it is understood that the present disclosure of the preferred forms is only by way of example and that numerous changes in the combination and arrangement of parts, as well as the details of the components, may be resorted to without departing from the spirit and scope of the invention as hereinafter claimed.

I claim:

1. A combination vault and storage cartridge for vials comprising a storage cartridge including a housing having a top wall providing at least one entry/exit opening for a vial, the at least one entry/exit opening being smaller than the top wall, a disc inside the housing and mounted for rotation about an axis, the disc having a multiplicity of sample holders for receiving vials having a machine readable tag, at least one of the sample holders being aligned with the at least one entry/exit opening in one rotational position of the disc, and a brake mounted in said housing for securing the disc against rotation, a vault including a docking station configured to removably receive the storage cartridge housing such that each said storage cartridge is selectively inserted into or retrieved from said docking station, means for activating the brake when the storage cartridge is out of the vault and releasing the brake at a time when the storage cartridge is in the vault to allow rotation of the disc when the storage cartridge is in the vault, said storage cartridge being configured to captivate the vials in the housing when the storage cartridge is out of the vault, the combination comprising a drive mechanism engaging the disc and adapted to rotate the disc about the axis, an input/output device movably mounted between a position aligned with the sample holder intersected by the entry/exit opening and a position for receiving a vial from a location beyond said vault, a control system configured to position the input/output device at selected ones of its positions, at least one conduit connected to said input/output device for transporting vials toward and away from the vault, and a reader for reading the machine readable tag.

2. The combination vault and storage cartridge of claim 1 further comprising a vial transfer station adjacent an end of the conduit and memory for storing data and wherein the input/output device is mounted for movement between the at least one entry/exit opening, the vial transfer station and the reader for picking up a vial, then moving the vial to a read position relative to the reader where the controller records information from the reader into memory, and then moving the vial to the at least one entry/exit opening and delivering the vial to the storage cartridge.

3. The combination vault and storage cartridge of claim 2 wherein the memory is in the storage cartridge.

4. The combination vault and storage cartridge of claim 1 wherein the input/output device is mounted for movement between the at least one entry/exit opening and the reader for retrieving a vial from the storage cartridge, then delivering the vial to the conduit.

5. The combination vault and storage cartridge of claim 1 wherein the drive mechanism, the input/output device and the control system are mounted on the vault.

6. The combination vault and storage cartridge of claim 1 wherein the only paths of vial movement into and out of the storage cartridge being through the at least one entry/exit opening.

7. The combination vault and storage cartridge of claim 1 further comprising a plurality of the storage cartridges adapted to be stored in a rack, wherein each storage cartridge housing is configured to be received in said docking station and includes a storage device, carried by the housing, including information about the vials, a communication link from the storage device to deliver information away from the storage cartridge, and whereby the storage cartridges are interchangeable between the vault and the rack.

8. The combination vault and storage cartridge of claim 7 further comprising memory, in the storage device, for storing data.

9. The combination vault and storage cartridge of claim 7 wherein the input/output device is mounted for movement between the at least one entry/exit opening and the reader for
retrieving a vial from the storage cartridge,
then delivering the vial to the conduit.

10. The combination vault and storage cartridge of claim 7 wherein the drive mechanism, the input/output device and the control system are in the vault and not in the storage cartridge.

11. The combination vault and storage cartridge of claim 7 wherein the only paths of vial movement into and out of the storage cartridge being through the at least one entry/exit opening.

12. The combination vault and storage cartridge of claim 7 wherein the arrangement of the at least one entry/exit opening and sample holders in the disc allows only one vial at a time to move through the at least one entry/exit opening.

13. The combination vault and storage cartridge of claim 1 wherein the sample holders are arranged in concentric circular rows and the at least one entry/exit opening overlies only one sample holder in any rotational position of the disc.

14. The combination vault and storage cartridge of claim 13 wherein the at least one entry/exit opening comprises at least one entry/exit opening for each row of sample holder.

15. The combination vault and storage cartridge of claim 13 wherein the at least one entry/exit opening comprises a slot intersecting a plurality of rows of sample holders.

16. The combination vault and storage cartridge of claim 1 wherein there is at least one rotational position of the disc where the at least one entry/exit opening is misaligned with all of the sample holders in the disc thereby preventing loss of a vial.

17. The combination vault and storage cartridge of claim 7 wherein the arrangement of the at least one entry/exit opening and sample holders in the disc allows only one vial at a time to move through the at least one entry/exit opening.

18. The combination vault and storage cartridge of claim 1 wherein the sample holders are arranged in concentric circles and the at least one entry/exit opening overlies only one sample holder in any one position of the disc.

19. The combination vault and storage cartridge of claim 7 wherein the sample holders are arranged in concentric circles and the at least one entry/exit opening overlies only one sample holder in any one position of the disc.

20. The combination vault and storage cartridge of claim 19 wherein the at least one entry/exit opening comprises at least one entry/exit opening for each row of sample holders.

21. The combination vault and storage cartridge of claim 19 wherein the at least one entry/exit opening comprises a slot intersecting a plurality of rows of sample holders.

22. The combination vault and storage cartridge of claim 7 wherein there is at least one relative position of the disc and at least one entry/exit opening where the at least one entry/exit opening is misaligned with all of the sample holders thereby preventing loss of a vial.

23. The combination vault and storage cartridge of claim 7 wherein the communication link is carried by the cartridge housing.

24. A combination vault and storage cartridges for vials comprising
first and second storage cartridges adapted to be stored in a rack, each storage cartridge including
a housing having a top wall providing at least one entry/exit opening for a vial having a machine readable tag, the at least one entry/exit opening being smaller than the top wall,
a disc inside the housing and mounted for rotation about an axis, the disc having a multiplicity of sample holders for receiving vials, each vial having a machine readable tag, and
a brake mounted in said housing configured to secure the disc against rotation, and
a vault including a docking station configured to removably receive each said storage cartridge housing such that each said storage cartridge is selectively inserted into or retrieved from said docking station, each cartridge being configured to retain all of the vials in the sample holders when the cartridge is out of a vault, the combination comprising
a drive mechanism engaging the disc and adapted to rotate the disc about the axis, an input/output device movably mounted between a first position aligned with the sample holder intersected by the entry/exit opening and a second position beyond said vault,
means for activating the brake when the first or second storage cartridge is out of the vault and releasing the brake at a time when the first or second storage cartridge is in the vault to allow rotation of the disc when the first or second storage cartridge is in the vault,
a reader for reading the machine readable tag, and
wherein the first and second storage cartridges are interchangeable between the vault and the rack.

25. The combination vault and storage cartridges of claim 24 further comprising
each storage cartridge further including
a storage device, carried by the housing, including information about the vials,
there being a communication link from the storage device to deliver information from the storage device away from the storage cartridge.

26. A combination vault and storage cartridge for vials comprising
a storage cartridge adapted to be inserted and removed to and from said vault including
a housing having a top wall providing at least one entry/exit opening for a vial, the at least one entry/exit opening being smaller than the top wall,
a disc inside the housing and mounted for rotation about an axis, the disc having a multiplicity of sample holders for receiving vials, the disc being configured to retain vials in the sample holders when the cartridge is outside a vault, and
a brake mounted in the housing and configured to secure the disc against rotation, and
said vault including a docking station configured to removably receive said storage cartridge housing such that said storage cartridge is selectively inserted into or retrieved from said docking station,
the combination comprising:
a drive mechanism configured to engage the disc and rotate the disc about the axis,
an input/output device movably mounted between a first position aligned with the sample holder intersected by the entry/exit opening and a second position receiving vials from a location beyond said vault, and
means for activating the brake when the first or second storage cartridge is out of the vault and releasing the brake at a time when the first or second storage cartridge is in the vault to allow rotation of the disc when the first or second storage cartridge is in the vault.

27. The combination vault and storage cartridge of claim 26 wherein the storage cartridge is a first cartridge and further comprising another storage cartridge adapted to be inserted and removed to and from said vault, said second cartridge including
- a second housing having a top wall providing at least one entry/exit opening for a vial, the at least one entry/exit opening being smaller than the top wall,
- a second disc inside the second housing and mounted for rotation about an axis, the second disc having a multiplicity of sample holders for receiving vials, the second disc being configured to retain vials in the sample holders when the second cartridge is outside a vault, and
- a second brake mounted in the second housing and configured to secure the second disc against rotation, and
- said second storage cartridge is configured to be selectively inserted into or retrieved from said docking station, and
- wherein the first and second storage cartridges are interchangeable between the vault and the rack.

* * * * *